United States Patent [19]

Wong et al.

[11] Patent Number: 5,278,299

[45] Date of Patent: Jan. 11, 1994

[54] METHOD AND COMPOSITION FOR SYNTHESIZING SIALYLATED GLYCOSYL COMPOUNDS

[75] Inventors: Chi-Huey Wong; Yoshitaka Ichikawa, both of San Diego; Gwo-Jenn Shen, Carlsbad, all of Calif.

[73] Assignee: Scripps Clinic and Research Foundation, La Jolla, Calif.

[21] Appl. No.: 670,701

[22] Filed: Mar. 18, 1991

[51] Int. Cl.$^5$ .................. C07H 1/00; C12N 9/12; C12N 9/24; C12P 19/26

[52] U.S. Cl. ...................... 536/53; 536/4.1; 536/26.14; 536/26.26; 536/26.8; 536/55.2; 536/55.3; 536/124; 435/84; 435/193; 435/194; 435/200; 424/94.2; 424/94.5; 424/94.61

[58] Field of Search ............. 536/4.1, 53, 55.3, 55.2, 536/124, 26.26, 26.14, 26.8; 514/25, 54; 435/84, 97, 193, 200, 194; 424/94.2, 94.5, 94.61

[56] References Cited

U.S. PATENT DOCUMENTS

| | | | |
|---|---|---|---|
| 4,918,009 | 4/1990 | Nilsson | 435/73 |
| 5,039,523 | 8/1991 | Payne et al. | 424/93 |
| 5,045,469 | 9/1991 | Payne et al. | 435/252.3 |

FOREIGN PATENT DOCUMENTS 3626915 2/1988 Fed. Rep. of Germany.
WO91/16449 10/1991 World Int. Prop. O..

OTHER PUBLICATIONS

Wong et al; J. Org. Chem. 47:5416–5418 (1982).
Holmes et al; J. Biol. Chem. 261(8):3737–43 (1986).
Tsuda et al., Eur. J. Biochem. 188:405 (1990).
Phillips et al., Science 250:1130 (1990).
Higa et al., J. Biol. Chem. 260(15):8838 (1985).
Gross et al., Eur. J. Biochem., 168:595 (1987).
Weinstein et al., J. Biol. Chem., 257(22):13845 (1982).
Schauer et al., Biochem. Soc. Symp., 40:87 (1974).
Sabesan, et al., J. Am. Chem. Soc. 108:2068 (1986).
Thiem, et al., Angew. Chem. Int. Ed. Engl. 25:1096 (1986).
Simon, et al., J. Am. Chem. Soc. 110:7159 (1988).

Auge, et al., Carbohydr. Res. 193:288 (1989).
Auge, et al., Carbohydr. Res. 200:257 (1990).
Palcic, et al., Carbohydr. Res. 190:1 (1989).
Beyer et al., Adv. Enzymol., 52:23 (1981).
Lowe, et al., Cell, 63:475 (1990).
Paulson, J. C., TIBS, 14:272 (1989).
Finne, J., TIBS, 129 (Mar. 1985).
Ernst et al., J. Biol. Chem., 264:3436 (1989).
Masibay et al., Proc. Natl. Acad. Sci. U.S.A., 86:5733 (1989).
Toghrol et al., Biochemistry, 29:2349 (1990).
Appert et al., EMBO, 9:3171 (1990).
Joziasse et al., Eur. J. Biochem., 191:75 (1990).
Vijay et al., J. Biol. Chem., 250(1):164 (1975).
Zapata et al., J. Biol. Chem., 264(25):14769 (1989).
Huse et al., Science, 246:1275 (1989).
Short et al., Nucleic Acids Res., 16:7583 (1988).
Van et al., J. Biol. Chem., 262:17556 (1987).

(List continued on next page.)

Primary Examiner—Nancy S. Husarik
Attorney, Agent, or Firm—Dressler, Goldsmith, Shore & Milnamow, Ltd.

[57] ABSTRACT

The present invention provides a method for synthesizing a sialylated glycosyl compound comprising reacting in the presence of each other a sialic acid, a glycosyl compound, a CMP-sialic acid regenerating system, a pyrophosphate scavenger and catalytic amounts of a CMP-sialic acid synthetase and a sialyl transferase having substrate specificity for the glycosyl compound. The present invention also provides a composition for sialylating glycosyl compounds comprising a sialic acid, CMP-sialic acid regenerating system, a pyrophosphate scavenger and a catalytic amount of CMP-sialic acid synthetase. The composition can further comprise an aqueous solvent having a suitable buffer and enzyme cofactors as well as a catalytic amount of a sialyl transferase having substrate specificity for the glycosyl compound. A phagemid-transformed E. coli that overproduces CMP-sialic acid synthetase is also disclosed.

24 Claims, 3 Drawing Sheets

OTHER PUBLICATIONS

David et al., *Adv. Carbohyd. Chem. Biochem.*, 49:175–237 (1991).
David et al., *Pure & Appl. Chem.*, 59(11):1501–1508 (1987).
Auge et al., *Tet. Lett.*, 29(7):789–790 (1988).
Borman, *C&EN*, 25–28 (Dec. 7, 1992).
Danishefsky, S. J. *J. Am. Chem. Soc.*, 111:6656 (1989).
Okamoto et al., *Tetrahedron*, 46:5835 (1990).
Ito et al., *Tetrahedron* 46:89 (1990).
Toone et al., *Tetrahedron*, 45:5365 (1989).
Schanbacher, et al., *J. Biol. Chem.*, 245:5057 (1970).
Berliner, et al., *Mol. Cell. Biochem.*, 62:37 (1984).
Nunez, et al., *Biochemistry*, 19:495 (1980).
Barker, et al., *J. Biol. Chem.*, 247:7135 (1972).
Babad, et al., *J. Biol. Chem.*, 241:2672 (1966).
Durrwachter et al., *J. Org. Chem.*, 1988, 53, 4175.
Pederson et al., *Tetrahedron Lett.* 1988, 29, 4645.
Von der Osten et al., *J. Am. Chem. Soc.* 1989, 111, 3924.
Pederson et al., *Heterocycles* 1989, 28, 477.
Pederson et al., *J. Org. Chem.* 1990 55, 489.
Weinreb et al., *Tetrahedron Lett.* 1986, 2099.
Paulson, et al., *3. Biol. Chem.*, 264:17615 (1989).
Aoki, et al., *EMBO*, 9:3171 (1990).
Shima, et al., *J. Ferm. Bioena.*, 68:75 (1989).
Ernst et al., *J. Biol. Chem.*, 264:3436 (1989).
Kajimoto, et al., *J. Am. Chem. Soc.*, in press.
Corey, et al., *J. Ora. Chem.*, 38:3224 (1973).
Schweden et al., *Arch. Biochem. Biophys.*, 1986, 248, 335.
Dale et al., *Biochemistry*, 1985, 24, 3530.
Ozaki et al., *J. Am. Chem. Soc.* 1990, 112, 4970.
Lowe et al., *Genes and Development*, 4:1288 (1990).
Tabor et al., *Proc. Natl. Acad. Sci. USA*, 82:1074 (1985).
Ichikawa et al., *J. Am. Chem. Soc.*, 113:4698 (1991).
Shames et al., *Glycobiology*, 1:87 (1991).
Kean et al., *Methods Enzymol.*, 8:208 (1966).
Roseman, S. *Proc. Natl. Acad. Sci.*, 48:437 (1962).
Gross et al., *Eur. J. Biochem.*, 117:583 (1988).
Zhong et al., *J. Am. Chem. Soc.*, 113:683 (1991).
Auge et al., *Tetrahed. Lett.*, 25:4663 (1984).
Kim et al., *J. Am. Chem. Soc.*, 110:6481 (1988).
Auge et al., *New J. Chem.*, 12:733 (1988).
Brossmer et al., *Biochem. Biophys. Res. Comm.*, 96:1282 (1980).
Auge et al., *Tetrahedron*, 46:201 (1990).
Auge et al., *Tetrahed. Lett.*, 30:2217 (1989).
Dumas et al., *Bioorg. Med. Chem*, 1:425 (1991).
Sharma et al., *Carb. Res.*, 175:25 (1988).

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

ATATTGAATT CTAAACTAGT CGCCAAGGAG ACAGTCATAA TGAGAACAAA AATTATTGCG 60

( 2 ) INFORMATION FOR SEQ ID NO:2:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

GCGCTCTAGA CTATTAAGAA CCGTAGTCCG GAACGTCGTA CGGGTATTTA ACAATCTCCG 60

CTATTTC 67

METHOD AND COMPOSITION FOR SYNTHESIZING SIALYLATED GLYCOSYL COMPOUNDS

This invention was made with government support under Contract GM 44154 awarded by the National Institutes of Health. The government has certain rights in the invention.

DESCRIPTION

1. Technical Field of the Invention

The present invention relates to a method and composition for synthesizing sialylated glycosyl compounds. In particular, this invention relates to an enzyme-catalyzed method for synthesizing sialylated glycosyl compounds involving the in situ regeneration of CMP-sialic acid.

2. Background of the Invention

Sialic acids conjugated to saccharides or to saccharides contained in glycoproteins or glycolipids have essential roles in a variety of biological processes. The removal of sialic acid from glycosylated erythropoietin completely abolishes the in vivo activity of this red blood cell maturation and growth factor. Tsuda et al., *Eur. J. Biochem.* 188:405 (1990). The adhesion of neutrophils to vascular endothelial cells via endothelial leukocyte adhesion molecule-1 (ELAM-1) is mediated by a sialylated carbohydrate ligand (sialyl-Lewis X), a structure found on neutrophil cell-surface glycoproteins and glycolipids. Phillips et al., *Science* 250:1130 (1990). In addition, sialylated oligosaccharides have been shown to be receptor determinants for a variety of ligands including animal viruses, mycoplasma, plant and animal lectins, bacterial toxins, interferon and certain tumor-specific and blood group-specific antibodies. Higa et al., *J. Biol. Chem.* 260(15):8838 (1985).

The attachment of sialic acid to a glycosyl compound involves the transfer of a sialic acid from an activated sialic acid compound to a glycosyl moiety in an acceptor molecule. This transfer of sialic acid is catalyzed by an enzyme known as a sialyl transferase. The activated sialic acid compound is a cytidine monophophate-sialic acid, or CMP-sialic acid. CMP-sialic acid is formed by reacting cytidine triphosphate (CTP) with sialic acid. The formation of CMP-sialic acid from CTP and sialic acid is catalyzed by an enzyme called CMP-sialic acid synthetase.

Currently available means of synthesizing sialylated glycosyl compounds involve a two step process. First, an activated sialic acid compound (CMP-sialic acid) is produced by reacting CTP with sialic acid in the presence of a CMP-sialic acid synthetase. Second, the activated sialic acid compound is then reacted with an acceptor glycosyl compound in the presence of a sialyl transferase. Such a two step process has been used to sialylate asialo-$\alpha_1$-acid glycoprotein [Gross et al., *Eur. J. Biochem.*, 168:595 (1987)], N-linked oligosaccharides [Weinstein et al., *J. Biol. Chem.*, 257(22):13845 (1982)] and O-linked oligosaccharides [Higa et al., *J. Biol. Chem.*, 260(15):8838 (1985)].

Such a two step synthetic procedure is inadequate, however, for the large scale preparation of sialylated glycosyl compounds. The production of activated sialic acid (CMP-sialic acid) is an expensive, time consuming process, which provides CMP-sialic acid only in low yields. Because CMP-sialic acid synthetase is not commercially available, it must be isolated and purified from animal tissues. About 500 grams of animal tissue are required to produce about 15 Units of the enzyme, an amount sufficient to generate only about 100 $\mu$mols of CMP-sialic acid. Higa et al., *J. Biol. Chem.* 260(15):8838 (1985). Further, the CMP-sialic acid so generated must be isolated and purified prior to use in a transferase reaction. Typically, such isolation and purification procedures involve the separate steps of alcohol extraction, silica-gel chromatography, desalting and analytical chromatography. Higa et al., *J. Biol. Chem.* 260(15):8838 (1985)..

Not only does the formation of CMP-sialic acid require large amounts of starting materials and extensive purification procedures but the reaction per se is self-limiting. Inorganic pyrophosphate, formed as a by-product of CMP-sialic acid synthesis, acts as a feed back inhibitor of CMP-sialic acid synthetase. Thus, that enzyme-catalyzed reaction for generating CMP-sialic acid can only be carried out for brief periods of time (minutes).

Because of these time and expense problems there is a pressing need for the development of new and efficient synthetic methods for preparing sialic acid derivatives. The present invention provides just such an efficient method by utilizing catalytic amounts of sugar nucleotides and nucleoside phosphates that are regenerated in situ.

BRIEF SUMMARY OF THE INVENTION

The present invention provides a method for synthesizing a sialylated glycosyl compound that comprises reacting in the presence of each other: a sialic acid; a glycosyl compound; a CMP-sialic acid regenerating system; a pyrophosphate scavenger; and catalytic amounts of a CMP sialic acid synthetase and a sialyl transferase having substrate specificity for the glycosyl compound.

The glycosyl compound is a monosaccharide, an oligosaccharide, a polysaccharide, a glycoprotein or a glycolipid.

The CMP-sialic acid regenerating system comprises CMP, a nucleoside triphosphate, a phosphate donor and catalytic amounts of a kinase and a nucleoside monophosphate kinase. Preferably, the nucleoside triphosphate is ATP, the phosphate donor is phosphoenolpyruvate and the kinase is pyruvate kinase.

CMP-sialic acid synthetase used in accordance with this synthetic method is preferably obtained from *E. coli* transformed with a CMP-sialic acid synthetase gene.

The sialyl transferase used in the synthetic method is a 2→3 transferase such as Sia$\alpha$2→3Gal, a 2→4 transferase such as Sia$\alpha$2→4Gal or Sia$\alpha$2→4GlcNAc, a 2→6 transferase such as Sia$\alpha$2→6Gal, Sia$\alpha$2→6GalNAc or Sia$\alpha$2→6GlcNAc or a 2→8 transferase such as Sia$\alpha$2→8Sia.

The method of synthesizing a sialylated glycosyl compound further preferably comprises isolating the sialylated glycosyl compound.

The present invention also provides a composition for synthesizing a sialylated glycosyl compound that comprises a sialic acid, a CMP-sialic acid regenerating system, a pyrophosphate scavenger and a catalytic amount of a CMP sialic acid synthetase. The composition of the present invention can exist as a dry formulation or as an aqueous solution. The composition can further comprise a sialyl transferase and cofactors for enzymes in the composition.

The present invention further provides an *E. coli* transformed with expression vector CMPSIL-1, which vector comprises a gene encoding CMP-sialic acid synthetase. The transformed *E. coli* has the ATCC designation 68531.

BRIEF DESCRIPTION OF THE DRAWINGS

In the figures which form a portion of this application.

DETAILED DESCRIPTION OF THE INVENTION

A. Method of Synthesizing a Sialylated Glycosyl Compound

One aspect of the present invention relates to a self-contained, cyclic method of synthesizing a sialylated glycosyl compound. In accordance with this method, there are reacted: a sialic acid; a glycosyl compound; a CMP-sialic acid regenerating system; a pyrophosphate scavenger, and catalytic amounts of a CMP-sialic acid synthetase and a sialyl transferase having substrate specificity for said glycosyl compound.

As used herein, the term "a sialic acid" means neuraminic acid (5-amino-3,5-dideoxy-D-glycero-D-galacto-2-nonulosonic acid), and derivatives such as an N- or O-acetyl derivative of neuraminic acid. Preferably, the sialic acid is an N-acetyl derivative of neuraminic acid (NeuAc), which has been reported as a naturally occurring sialic acid in various animal species Schauer, R., *Adv. Carbohydr. Chem. Biochem.*, 40:131 (1982).

A sialic acid derivative can be substituted at the carbon atom at positions 4, 5, 7, 8 or 9 of the sialic acid as herein defined. Exemplary derivatives at the above positions include a fluoro or deoxy group at positions 5, 7, 8 or 9, an $C_1$-$C_3$ acyl or amino acyl of an amino from an amino acid, and phosphoryl. Positions 5 or 9 can also be substituted with an azido group. Particularly preferred sialic acids are NeuAc, N-glycosylneuraminic acid, 9-O-acetyl-NeuAc, 9-deoxy-9-fluoro-NeuAc, and 9-deoxy-9-azido-NeuAc. A sialic acid used in accordance with the present invention can be obtained commercially (Sigma Chemical Company, St. Louis, Miss.) or isolated from various animal tissues. Schauer et al., *Biochem. Soc. Symp.*, 40:87 (1974).

As used herein, the term "a glycosyl compound" refers to an organic compound having one or more glycosyl residues. A "glycosyl residue" is a cyclic monosaccharide or monosaccharide derivative lacking the anomeric or glycosylic hydroxyl group. Preferred glycosyl residues are galactosyl (Gal), N-acetyl glucosyl (GlcNAc), N-acetyl galactosyl (GalNAc) and sialyl (Sia). The glycosyl residue acts as the acceptor site for the sialic acid, and therefore must have an appropriate hydroxyl group available to accept the sialic acid group. Acceptor glycosyl residues can exist as monosaccharides), oligosaccharides (containing from 2 to 9 monosaccharides), polysaccharides (containing 10 or more monosaccharides)k glycoproteins and glycolipids.

Examplary glycosyl compounds are listed in Table 1.

TABLE 1

| | Ref. |
|---|---|
| A. Saccharides | |
| Gal$\beta$OCH$_3$ | 1 |
| Gal$\beta$1, 4Glc$\beta$OCH$_3$ | 1 |
| Gal$\beta$1, 4GlcNAc | 1, 2-4 |
| Gal$\beta$1, 4GlcNAc$\beta$OCH$_3$ | 1 |
| Gal$\beta$1, 4GlcNAc$\beta$1, 3Gal$\beta$1, 4Glc | 1 |
| Gal$\beta$1, 4GlcNAc$\beta$1, 2Man$\alpha$OCH$_3$ | 6 |
| Glc$\beta$OCH$_3$ | 1 |
| GlcNAc$\beta$OCH$_3$ | 1 |
| GlcNAc$\beta$OR, R=CH$_2$Ph, —(CH$_2$)$_5$CO$_2$CH$_3$ | 1 |
| GlcNAc$\beta$1, 3Gal$\beta$1, 4Glc | 1 |
| Gal$\beta$1, 3GlcNAc$\beta$1, 3Gal$\beta$O(CH$_2$)$_8$CO$_2$Me | 7 |
| Gal$\beta$1, 3GlcNAc$\beta$1, 6Gal$\beta$O(CH$_2$)$_8$CO$_2$Me | 7 |
| B. Glycoproteins | |
| bovine submaxillary asialo mucin | 8 |
| bovine asialo fetuin | 8 |
| asialo epiglycanin | 8 |
| asialo human erythrocyte glycoprotein | 8 |
| asialo human chorionic gonadotropin | 8 |
| bovine asialo prothrombin | 8 |
| asialo transferrin | 8 |
| asialo antifreeze glycoprotein | 8 |
| Lewis X | 9 |
| human recombinant asialo erythropoietin | 10 |
| neutrophil adhesion molecule (N-CAM) | 11 |
| C. Glycolipids | |
| lactosylceramide | 8 |
| ganglioside G$_{M1}$ | 8 |
| hematoside (ganglioside G$_{M3}$) | 8 |
| D. Polysialic Acid | |
| colominic acid | 8 |
| brain glycans | 12 |
| bacterial capsular polysaccharides | 12 |

References
1. Sabesan, et al., J. Am. Chem. Soc. 108:2068 (1986)
2. Thiem, et al., Angew. Chem. Int. Ed. Engl. 25:1096 (1986)
3. David, et al., Pure Appl. Chem. 59:1501 (1987)
4. Simon, et al., J. Am. Chem. Soc. 110:7159 (1988)
5. Auge, et al., Carbohydr. Res. 193:288 (1989)
6. Auge, et al., Carbohydr. Res. 200:257 (1990)
7. Palcic, et al., Carbohydr. Res. 190:1 (1989)
8. Beyer et al., Adv. Enzymol., 52:23 (1981)
9. Lowe et al., Cell, 63:475 (1990)
10. Tsuda et al., Eur. J. Biochem., 188:405 (1990)
11. Paulson, J.C., TIBS, 14:272 (1989)
12. Finne, J., TIBS, 129 (March 1985)

As used herein, the term "pyrophosphate scavenger" refers to substances that serve to remove inorganic pyrophosphate from a reaction mixture of the present invention. Inorganic pyrophosphate (PPi) is a byproduct of CMP-sialic acid formation from CTP and sialic acid.

Normally, produced PPi feeds back to inhibit CMP-sialic acid synthetase such that CMP-sialic acid formation is reduced. However, PPi can be removed by metabolic means such as catabolism or by physical means such as sequestration by a PPi binding substance. Preferably, PPi is removed by metabolic means using inorganic pyrophosphatase, a commercially available PPi catabolic enzyme (Sigma Chem. Co., St. Louis, Miss.; Boehringer Mannheim, Indianapolis, Ind.), and that or a similar enzyme serves as the pyrophosphate scavenger.

A novel component of the method of the present invention is the in situ regeneration of CMP-sialic acid. The CMP-sialic acid regenerating system contemplated by the present invention comprises cytidine monophosphate (CMP), a nucleoside triphosphate, a phosphate donor, a kinase capable of transferring phosphate from the phosphate donor to nucleoside diphosphates and a nucleoside monophosphate kinase capable of transferring the terminal phosphate from a nucleoside triphosphate to CMP.

Nucleoside triphosphates suitable for use in accordance with the CMP-sialic acid regenerating system are adenosine triphosphate (ATP), cytidine triphosphate (CTP), uridine triphosphate (UTP), guanosine triphosphate (GTP), inosine triphosphate (ITP) and thymidine triphosphate (TTP). A preferred nucleoside triphosphate is ATP.

The phosphate donor of the CMP-sialic acid regenerating system is a phosphorylated compound, the phosphate group of which can be used to phosphorylate a nucleoside diphosphate such as ADP or CDP. The only limitation on the selection of a phosphate donor is that neither the phosphorylated nor the dephosphorylated forms of the phosphate donor can substantially interfere with any of the reactions involved in the formation of the sialylated glycosyl compound. Preferred phosphate donors are phosphoenolpyruvate (PEP) and acetyl phosphate. A particularly preferred phosphate donor is PEP.

Kinases catalyze the phosphorylation of proteins or nucleoside diphosphates. As used herein, the term "kinase" refers to those members of the kinase family that are capable of transferring a phosphate group from a phosphate donor to nucleoside diphosphates such as ADP or CDP.

The selection of a particular kinase for use in accordance with the present invention depends upon the phosphate donor employed. When acetyl phosphate is used as the phosphate donor, the kinase is acetyl kinase. When PEP is used as the phosphate donor, the kinase is pyruvate kinase. Other kinases can be employed with other phosphate donors as is well known to those of skill in the art. Kinases are commercially available (Sigma Chem. Co., St. Louis, Miss.; Boehringer Mannheim, Indianapolis, Ind.).

Nucleoside monophosphate kinases are enzymes that catalyze the phosphorylation of nucleoside monophosphates. Nucleoside monophosphate kinase (NMK) used in accordance with the CMP-sialic acid regenerating system of the present invention is used to catalyze the phosphorylation of CMP. NMK's are commercially available (Sigma Chem. Co., St. Louis, Miss.; Boehringer Mannheim, Indianapolis, Ind.).

Figure 1:
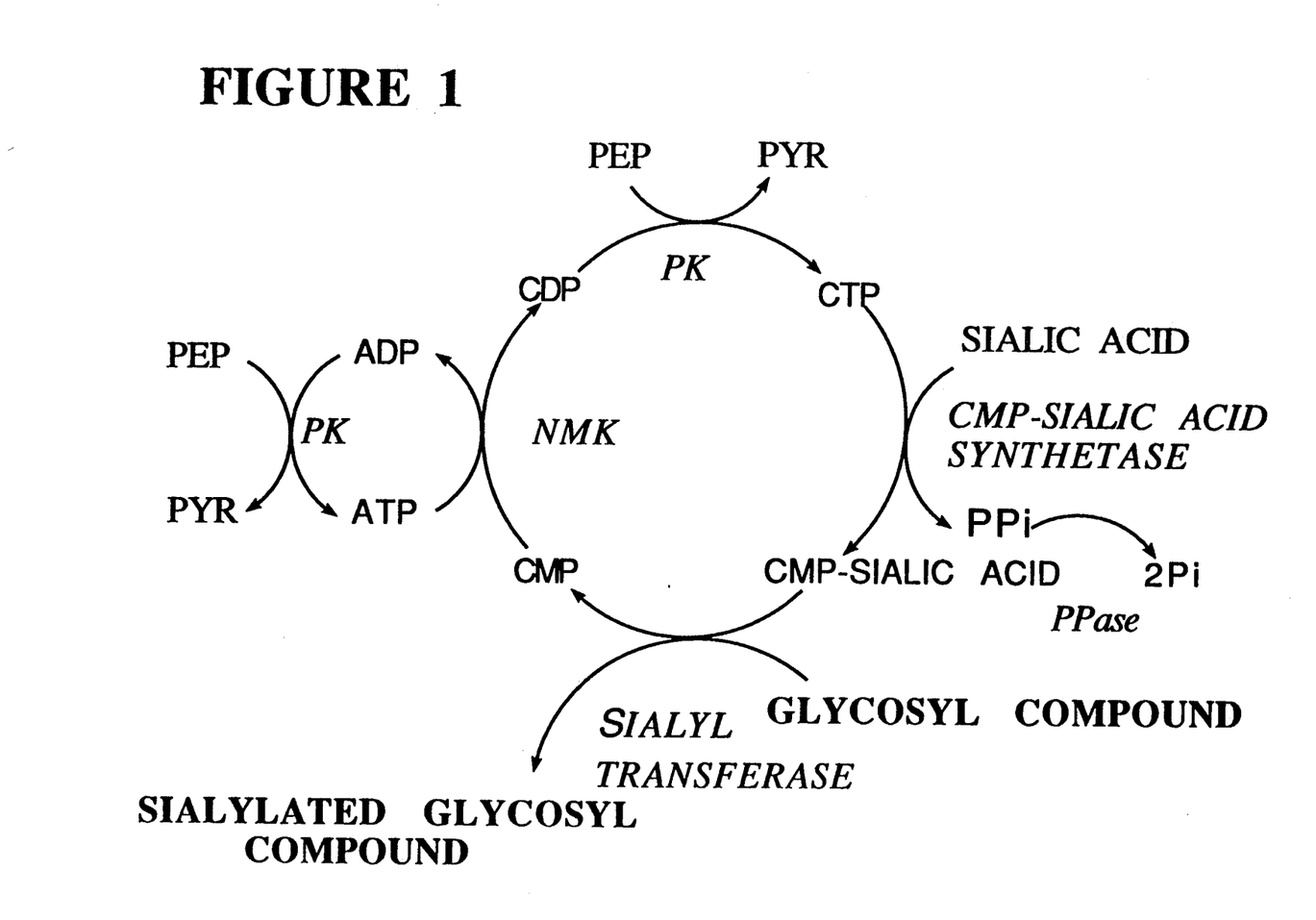
FIG. 1 is a schematic diagram of a CMP-sialic acid regenerating system. CMP, CDP and CTP are cytidine monophosphate, cytidine diphosphate and cytidine triphosphate respectively. ADP and ATP are adenosine diphosphate and adenosine triphosphate, respectively. PEP and PYR are phosphoenolpyruvate and pyruvate, respectively. PPi is inorganic pyrophosphate. PK is pyruvate kinase. NMK is nucleoside monophosphate kinase. PPase is inorganic pyrophosphatase.

A preferred embodiment for a CMP-sialic acid regenerating system of the present invention is schematically diagrammed in FIG. 1. Examination of FIG. 1 shows the self-contained and cyclic character of this synthetic method whereby once all the reactants and enzymes are present, the sialylation reaction continues until the first of the phosphate donor, sialic acid or glycosyl compound is consumed.

Thus, CMP is converted to CDP, which conversion is catalyzed by nucleoside monophosphate kinase in the presence of added ATP. ATP is catalytically regenerated from its byproduct, ADP, by pyruvate kinase (PK) in the presence of added phosphoenolpyruvate (PEP). CDP is further converted to CTP, which conversion is catalyzed by PK in the presence of PEP. CTP reacts with sialic acid to form PPi and CMP-sialic acid, the latter reaction being catalyzed by CMP-sialic acid synthetase. Following sialylation of the glycosyl compound, the released CMP re-enters the regenerating system to reform CDP, CTP and CMP-sialic acid. The formed PPi is scavenged as discussed before, and forms inorganic phosphate (Pi) as a byproduct. Pyruvate (PYR) is also a byproduct.

Sialyl transferases catalyze the transfer of a sialic acid moiety from an activated sialic acid (CMP-sialic acid) to a glycosyl compound, which serves as a substrate for the transferase enzyme. Sialyl transferase enzymes are substrate specific. Thus, the selection of a particular sialyl transferase depends upon the nature of the glycosyl compound (substrate) to be sialylated, and the desired sialylated product.

The substrate specificity of a sialyl transferase is dependent upon both the chemical structure of the glycosyl compound and the availability of a hydroxyl group of a particular carbon atom within such compound that serves as the acceptor site for the sialic acid. Exemplary glycosyl chemical structures as contained in the compounds listed in Table 1 include galactosyl, sialyl, N-acetylgalactosyl (GalNAc) and N-acetylglucosyl (GlcNAc).

Sialyl transferases can sialylate glycosyl compounds at the hydroxyl group of the carbon atom at position 3, 4, 6, or 8 of the particular glycosyl compound serving as substrate. Thus, a 2→3 sialyl transferase catalyzes the sialylation of the carbon atom hydroxyl at position 3 of a substrate glycosyl compound. Other types of sialyl transferases are referred to herein as 2→4, 2→6 and 2→8 sialyl transferases. The sialic acid moiety is attached to the glycosyl compound via the carbon atom at position number 2 of the sialic acid moiety.

Specific sialyl transferases are named according to their substrate specificity. Thus, a sialyl transferase designated Siaα2→6Gal refers to a sialyl transferase that catalyzes the transfer of sialic acid to the hydroxyl group at position number 6 of a galactosyl compound. Exemplary sialyl transferases are (1) Siaα2→6Gal, (2) Siaα2→3Gal, (3) Siaα2→6GalNAc, (4) Siaα2→6GlcNAc, (5) Siaα2→4Gal, (6) Siaα2→4GlcNAc and (7) Siaα2→8Sia. Beyer et al., *Advances in Enzymology*, 52: 28–44 (1981).

Sialyl transferases catalyze the sialylation of glycosyl compounds in the form of a mono-, oligo- or polysaccharide as well as a mono-, oligo- or polysaccharide conjugated to a protein or a lipid to form a glycoprotein or a glycolipid, respectively. For example, Siaα2→3Gal transferase has been shown to catalyze the sialylation of glycoproteins, glycolipids and oligosaccharides. Beyer, supra.

Sialyl transferase enzymes are commercially available (Sigma Chemical Company, St. Louis, Miss.; Boehringer Mannheim, Indianapolis, Ind. and Genzyme Cambridge, Mass.). Alternatively, sialyl transferases are isolated and purified from animal tissues such as bovine submaxillary gland and rat liver. See e.g., Gross et al., Eur. J. Biochem., 168:595 (1987) and Higa et al., J. Biol. Chem.. 260(15):8838 (1985). In addition, sialyl transferases are available in recombinant form. See e.g., Ernst et al., J. Biol. Chem., 264:3436 (1989); Masibay et al., Proc. Natl. Acad. Sci. U.S.A., 86:5733 (1989); Toghrol et al., Biochemistry, 29:2349 (1990); Appert et al., EMBO, 9:3171 (1990) and Joziasse et al., Eur. J. Biochem., 191:75 (1990).

CMP-sialic acid synthetase catalyzes the formation of CMP-sialic acid from CTP and sialic acid. CMP-sialic acid synthetase used in accordance with the present invention can be isolated and purified from cells and tissues containing the synthetase enzyme by procedures well known in the art. See, e.g., Gross et al., Eur. J. Biochem., 168:595 (1987); Vijay et al., J. Biol. Chem., 250(1):164 (1975); Zapata et al., J. Biol. Chem., 264(25):14769 (1989) and Higa et al., J. Biol. Chem., 260(15):8838 (1985).

In one embodiment, grey matter from bovine brain is homogenized, the homogenate centrifuged to form a pellet and a supernatant, and the supernatant lyophilized to yield a powder. The lyophilized powder is reconstituted in distilled water, homogenized and centrifuged to yield a supernatant and a fluffy pellet containing the CMP-sialic acid synthetase. The synthetase enzyme is double extracted from the fluffy pellet with KCl to yield a semi-purified extract. Contaminating amounts of nucleoside phosphatase and O-acetyl esterase are removed from the semi-purified extract by sequential ammonium sulfate precipitation and dialysis. Higa et al., J. Biol. Chem. 260(15):8838 (1985).

In another embodiment, CMP-sialic synthetase is obtained from transformed host cells using genetic engineering and recombinant DNA technologies. One such method for obtaining CMP-sialic acid synthetase has been reported by Zapata et al., J. Biol. Chem. 264(25):14769 (1989). In this embodiment, plasmid pSR35 containing the E. coli CMP-sialic acid synthetase gene is digested with Eco RI and Hind III to yield a 2.7 kb fragment, which is inserted into Eco RI-Hind III digested vector pKK223-3 (Pharmacia LKB Biotechnology Inc.) to form plasmid pWA1. Plasmid pWA1 is then used to transform E. coli. The transformed E. coli are reported to express CMP-sialic synthetase to a level 10-30 fold higher than in non-transformed bacteria. Zapata et al., J. Biol. Chem. 264(25):14769 (1989).

In a preferred embodiment, CMP-sialic acid synthetase is obtained from host cells transformed with a novel bacteriophage lambda vector system recently described by Huse et al., Science, 246:1275 (1989). A detailed description of this method for obtaining CMP-sialic acid synthetase is set forth in Example 2.

According to one aspect of this preferred embodiment, genomic DNA is extracted from E. coli strain K235 (ATCC 13207), and the gene for CMP-sialic acid synthetase is isolated via polymerase chain reaction (PCR) amplification in the presence of two custom-designed polynucleotide primers (see Example 2). One primer contains an Eco RI restriction site, a ribosomal binding sequence, a start codon, and an oligonucleotide corresponding to the N-terminal hexapeptide of the enzyme. The second primer contains, from 3' to 5', an Xba I restriction site, a stop codon, a decapeptide tag sequence, and a sequence corresponding to the C-terminal heptapeptide of the enzyme. The amplified gene was cloned into a lambda ZAP TM (Stratagene Cloning Systems, La Jolla, Calif.) vector at the Eco RI and Xba I sites for the construction of a phagemid for expression of the enzyme in E. coli.

It was particularly surprizing that DNA coding for an emzyme as large as CMP-sialic acid synthetase could be successfully cloned into and translated from this phage vector. Prior reports had only described use of DNA coding for an antibody Fab fragment (about 50,000 kd), which is about 15-20 percent of the size of the present DNA and protein.

Transformed E. coli produce approximately 100 U/L of CMP-sialic acid synthetase compared to <0.1 U/L for the wild-type, non-transformed strain, corresponding to a >1,000-fold increase of enzyme activity. Such a transformed E. coli was deposited on Feb. 19, 1991 with the American Type Culture Collection, Rockville, Md. and assigned ATCC accession No 68531.

The above deposit was made in compliance with the Budapest Treaty requirements that the duration of the deposit should be for 30 years from the date of deposit or for 5 years after the last request for the deposit at the depository or for the enforceable life of a U.S. Patent that matures from this application, whichever is longer. The cells will be replenished should they become nonviable at the depository, and will be made available to the public by the ATCC upon the issuance of a patent from this application.

The concentration or amount of the various reactants used in the sialylation method of the present invention depend upon numerous factors including reaction conditions such as temperature and pH value, and the amount of glycosyl compound to be sialylated. Because the sialylation method of the present invention permits regeneration of CMP, CDP, CTP, ADP, ATP and CMP-sialic acid and scavenging of produced PPi in the presence of catalytic amounts of the enzymes, the method is limited by the concentrations or amounts of sialic acid, phosphate donor and glycosyl compound. The upper limit for the concentrations of reactants that can be used in accordance with the method of the present invention is determined by the solubility of such reactants.

In a preferred embodiment, sialylation is limited by the concentration of sialic acid. According to such an embodiment, the concentrations of CMP, nucleoside triphosphate, phosphate donor, glycosyl compound and enzymes are selected such that sialylation of the glycosyl compound proceeds until sialic acid is consumed.

When the concentration of sialic acid is about 20 mM, preferred concentrations of the other non-enzyme reactants are about 20 mM for the glycosyl compound, about 20–200 $\mu$M for CMP, about 2–20 $\mu$M for the nucleoside triphosphate and about 40 mM for the phosphate donor. Thus, the ratio of the concentration of these reactants to the concentration of sialic acid is preferably about 0.01–0.1:1 for the glycosyl compound, about 0.001–0.01:1 for CMP, about 0.01–0.001:1 for the nucleoside triphosphate and about 2:1 for the phosphate donor.

All enzymes are present in catalytic amounts. As used herein, "catalytic amount" means that amount of an enzyme at least sufficient to catalyze, in a non-rate-limiting manner, the conversion of that enzyme's substrate to product. The catalytic amount of a particular enzyme varies according to concentration of that enzyme's substrate as well as to reaction conditions such as temperature, time and pH value. Means for determining the catalytic amount of a particular enzyme under preselected substrate concentrations and reaction conditions are well known to those of skill in the art.

Enzyme amounts or concentrations are expressed in activity Units. One activity Unit catalyzes the formation of 1 μmol of product at a given temperature (typically 37° C.) and pH value (typically 7.5) per minute. Thus, 10 Units of an enzyme is a catalytic amount of that enzyme where 10 μmols of substrate are converted to 10 μmols of product in one minute at a temperature of 37° C. and a pH value of 7.5.

Reacting comprises mixing each listed ingredient with each of the other ingredients in a suitable aqueous solvent to form a reaction mixture and maintaining the reaction mixture under biological reaction conditions of temperature, pH value, solvent osmolality, ionic composition and ambient atmosphere for a period of time sufficient to consume the sialic acid, phosphate donor or glycosyl compound.

The selection of particular conditions depend primarily upon the amount of glycosyl compound to be sialylated. Temperature can range from about 15° C. to about 40° C. Preferably temperature is from about 20° C. to about 30° C. and, more preferably about 25° C.

The pH value can range from about 6.0 to about 11.0. Preferably, the pH value is from about 6.5 to about 8.5 and, more preferably about 7.0 to about 7.5. The pH value is maintained by buffers in the aqueous solvent. The buffer is devoid of phosphate, EDTA, EGTA and other chelators that bind Mg or Mn. The selection of a buffer is based on the ability of the buffer to maintain pH value at the desired level. Where the pH value is about 7.5, a preferred buffer is HEPES.

The osmolality and ionic composition of the aqueous solvent are designed and selected to solubilize the ingredients of the reaction mixture and to provide cofactors for the enzymes contained in the reaction mixture. For example, CMP-sialic acid synthetase requires metal ions such as $Mg^+$ for optimal activation and Mn to shift the pH value optimum of CMP-sialic acid synthetase toward neutral pH values of from about 7 to about 8. Higa et al., *J. Biol. Chem.* 260(15):8838 (1985). In addition, $Mn^{2+}$ ions prevent inhibition of sialyl transferase by CDP. Weinstein, et al., *J. Biol. Chem.*, 257(22):13845 (1982).

In a preferred embodiment, where the pH value of the reaction mixture is about 7.5, the aqueous solvent comprises from about 1 to about 5 mM $MgCl_2$ and from about 0.4 to about 1.5 mM $MnCl_2$. The osmolality of the aqueous solvent including the buffer is preferably from about 100 mOsm to about 300 mOsm.

The sialylation method of the present invention preferably further comprises isolating the sialylated glycosyl compound. Isolating comprises recovering the sialylated glycosyl compound from the reaction mixture. Means for recovering the sialylated glycosyl compound include gel filtration, column chromatography, paper chromatography, affinity chromatography, extraction, precipitation and the like.

In a preferred embodiment, isolation is accomplished by lyophilizing the reaction mixture to reduce the volume of the reaction mixture, applying the lyophilized reaction mixture to a gel filtration column of about 200–400 mesh and eluting the sialylated glycosyl compound from the filtration column. Where such an embodiment is used to isolate sialylated glycosyl compounds, such compounds can be recovered with a yield of about 97 percent (see Example 1).

B. Sialylation Composition

Another aspect of the present invention relates to a composition for sialylating glycosyl compounds. Such a sialylation composition comprises a sialic acid, a CMP-sialic acid regenerating system, a pyrophosphate scavenger and a catalytic amount of CMP-sialic acid synthetase.

The sialylation composition can exist in the form of dry ingredients or in the form of an aqueous solution comprising solubilized ingredients. The aqueous solvent can further comprise a suitable buffer and cofactors for optimizing enzyme activity as well as a catalytic amount of a sialyl transferase enzyme having substrate specificity for said glycosyl compound.

The nature of each ingredient in the sialylation composition is the same as defined above in relation to the sialylation methods.

The amounts or concentrations of each ingredient of the sialylation composition can vary in accordance with the intended use of such composition. The only limitation being that the amounts or concentrations of the ingredients are sufficient to sialylate a preselected amount of a glycosyl compound.

For example, where about 5 mmols of a glycosyl compound are to be sialylated, the sialylation composition preferably comprises at least about 5 mmols of a sialic acid, about 50–500 μmols of CMP, about 5–50 μmols of a nucleoside triphosphate, about 10 mmols of a phosphate donor and catalytic amounts of a kinase, a nucleoside monophosphate kinase, an inorganic pyrophosphatase, a sialyl transferase and a CMP-sialic acid synthetase. The catalytic amounts of the various enzymes depend upon the temperature and pH value at which the composition is to be used as defined above. Where sialylation proceeds at a temperature of about 25° C. and at a pH value of about 7.5, and where the sialylation composition comprises about 5 mmols of a sialic acid, preferred catalytic amounts of the various enzymes are about 10,000 Units of the kinase, about 750 Units of the nucleoside monophosphate kinase, about 500 Units of the inorganic pyrophosphatase, about 5 Units of sialyl transferase and about 40 Units of the CMP-sialic acid synthetase.

The following examples illustrate particular embodiments of the present invention and are not intended to be limiting of the specification and claims in any way.

EXAMPLE 1

Synthesis of Sialyl N-Acetyllactosamine

Sialyl N-acetyllactosamine (NeuAcα2,6Galβ1,4GlcNAc) was synthesized in an enzyme-catalyzed method with the in situ regeneration of CMP-sialic acid according to scheme 1 shown below.

According to this scheme, CMP was converted to CDP catalyzed by nucleoside monophosphate kinase (NMK) in the presence of ATP, which was regenerated from its byproduct ADP catalyzed by pyruvate kinase (PK) in the presence of PEP. CDP was further converted to CTP with PEP catalyzed by PK. CTP reacted with NeuAc catalyzed by CMP-NeuAc synthetase to produce CMP-NeuAc. The byproduct inorganic pyrophosphate was scavenged by pyrophosphatase (PPase). Sialylation of Galα1,4GlcNAc was accomplished by CMP-NeuAc and Siaα2→6Gal sialyl transferase. The released CMP was again converted to CDP, to CTP and to CMP-NeuAc.

Neuraminic acid (NeuAc), CMP, ATP, PEP (monosodium salt), MgCl$_2$.6H$_2$O, MnCl$_2$.4H$_2$O, KCl, pyruvate kinase (PK, EC 2.7.1.40), nucleoside monophosphate kinase (NMK, EC 2.7.4.4) and inorganic pyrophosphatase (PPase, EC 3.6.1.1) were purchased from Sigma Chemical Co., St. Louis, Miss.. Siaα2→6Gal sialyl transferase (EC 2.4.99.1) was obtained as a generous gift and can be purchased from Sigma Chemical Co., St. Louis, Miss. CMP-NeuAc synthetase (EC 2.7.7.43) was obtained from E. coli transformed with a CMP-NeuAc gene according to the method of Example 2.

NeuAc (0.92 g, 3 mmol), Galβ1,4GlcNAc (1.1 g, 3 mmol), CMP (0.1 g, 30μmol), ATP (16 mg, 3μmol), PEP (2.8 g, 6 mmol), MgCl$_2$.6H$_2$O (0.61 g, 3 mmol), MnCl$_2$.4H$_2$O (0.15 g, 0.8 mmol), KCl (0.22 g, 3 mmol), NMK (450 U), PK (6,000 U), PPase (300 U), CMP-NeuAc synthetase (24 U), and Siaα2→6Gal sialyl transferase (4 U) were mixed with 150 ml of HEPES buffer (0.2M, pH 7.5) to form a reaction mixture and the reaction mixture maintained under argon at about 25° C. for about 48 hours. After the disappearance of NeuAc (determined by thin-layer chromatography) the reaction mixture was reduced in volume to 20 ml by lyophilization and the lyophilized reaction mixture applied to a Bio Gel P2 (200–400 mesh) column with water as the mobile phase. The trisaccharide-containing fractions were eluted, collected and lyophilized to give pure Neuα2,6Galβ1,4GlcNAc in 97 percent yield.

$^1$H-NMR: 1.701 (1H, t, J=12.5 Hz, H-3$_{ax}$ of NeuAc), 2.007 (3H, s, NHAc of GlcNAc), 2.004 (3H, s, NHAc of NeuAc), 2.649 (1H, dd, J=5.0 and 12.5 Hz, H-3$_{eq}$ of NeuAc, 4.43 1,d, J=8.0 Hz, H-1 of Gal), 4.73 (0.5H, d, J=8.0 Hz, H-1b of GlcNAc), and 5.178 (0.5H, d, J=2.5 Hz, H-1a of GlcNAc).

The turn-over number for ATP was about 1000 and that of CMP, CDP, CTP and CMP-NeuAc was about 100.

These data show that a glycosyl compound can be sialylated in an efficient, enzyme-catalyzed, self-contained, cyclic, synthetic method involving the in situ regeneration of CMP-sialic acid. This synthetic method provides a novel, high-yield (97 percent) scheme for the large-scale preparation of sialylated glycosyl compounds.

EXAMPLE 2

Preparation of Recombinant CMP-NeuAcSynthetase

The gene coding for CMP-N-acetylneuraminic acid (CMP-NeuAc) synthetase (EC 2.7.7.43) was amplified from total DNA of E. coli strain K-235 through a primer-directed polymerase chain reaction. The gene was fused with a modified ribosome binding site of the original CMP-NeuAc synthetase gene and a decapeptide tag sequence which served as a marker for screening of expressed proteins. The gene was cloned into lambda ZAP TM vector at Eco RI and Xba I sites and overexpressed in E. coli Sure at a level approximately 1000 times that of the wild type.

E. coli strain K235 (ATCC 13207) was obtained from American Type Culture Collection and maintained on LB (Luria-Bertani) medium (one liter contains: Bacto Tryptone, 25g; Yeast extract, 10 g; NaCl, 3 g: pH 7.0). Genomic DNA was extracted from the E. coli according to the method described by Maniatis et al., Molecular Cloning: A Laboratory Manual, Cold Spring Harbor Laboratory, Cold Spring Harbor, N.Y. (1989).

The CMP-NeuAc synthetase gene was isolated via PCR amplification in the presence of two custom-designed primers (Table 2).

TABLE 2

Primer CMP5

5' ATATT<u>GAATTC</u>TAAACTAGTCG<u>CCAAGGAGACA</u>GTCATA<u>ATGAGA</u>
        Eco RI           Shine Dalgarno      Start <u>ACAAAAATTATTGCG</u> 3'    (Sequence I.D. No. 1)
gene N-terminal Primer CMP3

5' GCG<u>CTCTAGA</u>CTATTA<u>AGAACCGTAGTCCGGAACGTCGTACGGG</u>
    Xba I stop         Decapeptide tag

TABLE 2-continued

T<u>ATTTAACAATCTCCGCTATTTC</u> 3'    (Sequence I.D. No. 2)
   gene C-terminal Primer CMP5 contained an ECO RI restriction site, a ribosomal binding sequence, a start codon and an oligonucleotide corresponding to the N-terminal hexapeptide of the enzyme (underlined above). Primer CMP3 contained an Xba I restriction site, a stop codon, a decapeptide tag sequence and a sequence corresponding to the C-terminal heptapeptide of the enzyme (also underlined above).

PCR amplification was performed in a 100 μL reaction mixture containing 2 μL (2 μg) of E. coli strain K235 DNA, 400 nmol of primers CMP5 and CMP3, 200 μM of different dNTPs, 50 mM KCl, 10 mM Tris-HCl (pH 8.3), 2 mM $MgCl_2$, 0.01 percent (w/v) gelatin, 0.1 percent (v/v) Triton X-100, and 2 units of *Thermus acuaticus* DNA polymerase. The reaction was overlaid with mineral oil and subjected to 35 cycles of amplification. The cycle conditions were set as denaturation at 94° C. for 1 minute, annealing at 60° C. for 2 minutes, and elongation at 72° C. for 1.5 minutes. The primers were annealed with E. coli DNA at 94° C. for 2 minutes followed by slow cooling to room temperature prior to PCR amplification.

The amplified gene was cloned into lambda ZAP TM II vector at the Eco RI and Xba I sites for the construction of phagemid for expression of the enzyme in E. coli.

Lambda Zap TM II is a derivative of the original Lambda Zap TM vector (ATCC #40,298) that maintains all of the characteristics of the original Lambda Zap TM including 6 unique cloning sites, fusion protein expression, and the ability to rapidly excise the insert in the form of a phagemid (Bluescript SK-), but lacks the SAM 100 mutation, allowing growth on many Non-Sup F strains, including XL1-Blue. The Lambda Zap TM II vector was constructed as described by Short et al., [*Nucleic Acids Res.*, 16:7583 (1988)] by replacing the Lambda S gene contained in a 4254 base pair (bp) DNA fragment produced by digesting Lambda Zap TM with the restriction enzyme Nco I. This 4254 bp DNA fragment was replaced with the 4254 bp DNA fragment containing the Lambda S gene isolated from Lambda gt10 (ATCC #40,179) after digesting the vector with the restriction enzyme Nco I. The 4254 bp DNA fragment isolated from lambda gt10 was ligated into the original Lambda Zap TM vector using T4 DNA ligase and standard protocols for such procedures described in *Current Protocols in Molecular Biology*, Ausubel et al., eds., John Wiley and Sons, NY, 1987.

Figure 2:
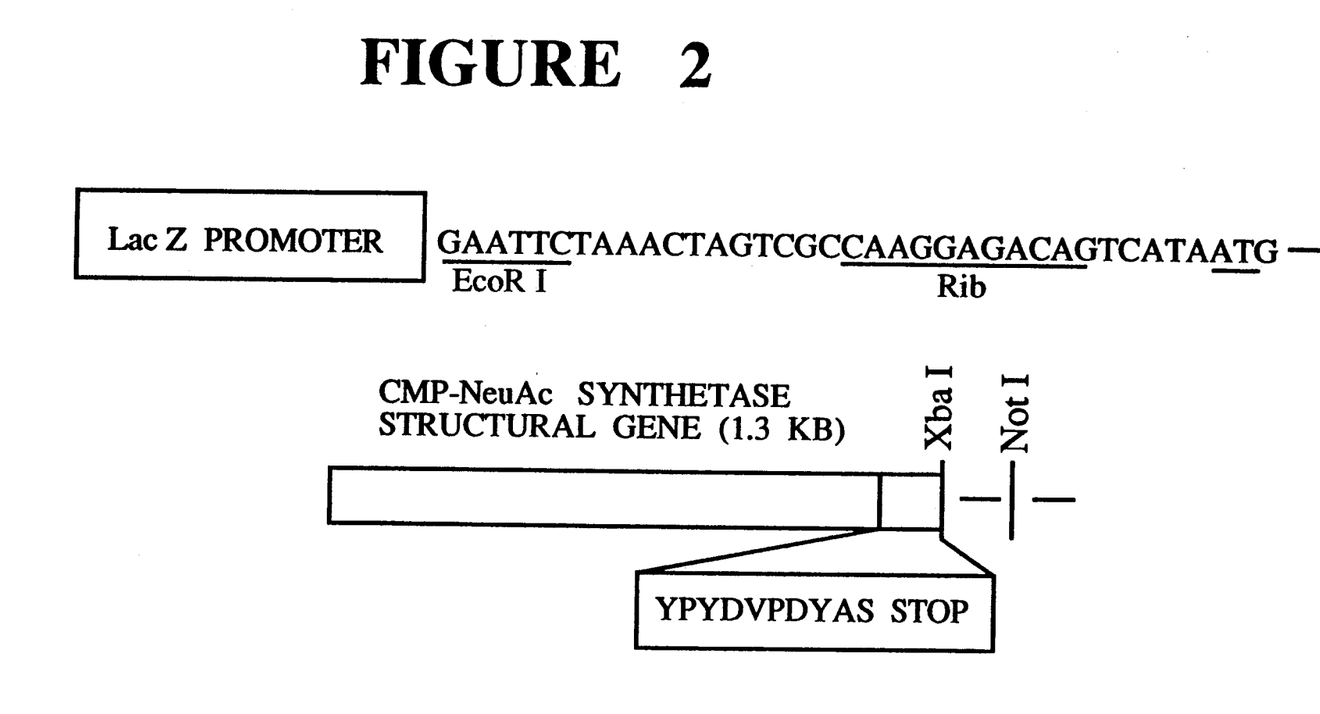
FIG. 2 is a schematic diagram showing the construction of the DNA insert containing the 1.3kb PCR amplification product that includes the CMP-NeuAc synthetase structural gene as well as the upstream Lac Z promoter and linking DNA having an Eco RI restriction site (underlined), a ribosome binding site (Rib, sequence underlined) and an ATG (underlined) start signal, and the downstream amino acid residue sequence of the tag peptide and DNA stop signal (boxed), followed downstream by Xba I and Not I restriction sites, and the arms from lambda Lcl vector according to Example 2.

The DNA obtained from the PCR amplification was purified on 0.6 percent agarose gel. The DNA band corresponding to 1.3 kb was separated from the agarose and electro-eluted. The DNA was then extracted with phenol/chloroform and precipitated with ethanol overnight at 20° C. The precipitated DNA was disclosed in a proper restriction enzyme buffer supplied by Boehringer Mannheim Biochemical Co. (Indianapolis, Ind.) and digested with 40 units/μg DNA of Eco RI and Xba I at 37° C. for 2 hours. The digested DNA was then recovered by phenol/chloroform extraction and ethanol precipitation and resuspended in a TE buffer (pH 7.5). This DNA was used as an insert. The arms were also prepared from the digestion of vector lambda Lcl with 20 Units/mg DNA of Eco RI and Xba I and recovered with ethanol precipitation after extraction with phenol/chloroform. Vector lambda LcI was obtained as a generous gift from Dr. R. A. Lerner (Scripps Clinic and Research Foundation, La Jolla, Calif.). The insert was then ligated with the arms and packaged with a packaging kit as suggested by the manufacturer (Stratagene Co., San Diego, Calif.). The PCR amplification product insert with lambda Lcl arms is shown in FIG. 2.

After packaging, the phage solution was used to infect host strain XL1-Blue (Stratagene Co., San Diego, Calif.) and plated on LB agar plates at 37° C. After plaque formation was observed, a nitrocellulose membrane previously soaked with 0.5 mM IPTG (Isopropyl-β-D-thiogalactopyranoside) solution was carefully placed on the top of the agar and incubated at 25° C. overnight (about 15 hours). The nitrocellulose membrane was then used for screening with alkaline phosphatase conjugated with the anti-decapeptide tag antibody. Positive clones with intense blue color plaques were cored from the agar plates and transferred to sterile microfuge tubes containing 500 μL of SM buffer and 20 μl of $CHCl_3$. For extension, 200 μl of the phase stock was mixed with 200 μL of LX1-Blue cells ($OD_{660}=1.0$) and 2 μL of R408 helper phage ($1 \times 10^{11}$ pfu/ml from Stratagene Co.), and the mixture incubated at 37° C. for 10 minutes. Excised plasmids were used to infect XL1-Blue cells [Short et al. *Nucleic Acids Res.*, 16:7583 (1988)], plated, and analyzed for expression of the enzyme by ELISA and enzyme activity assays.

Figure 3:
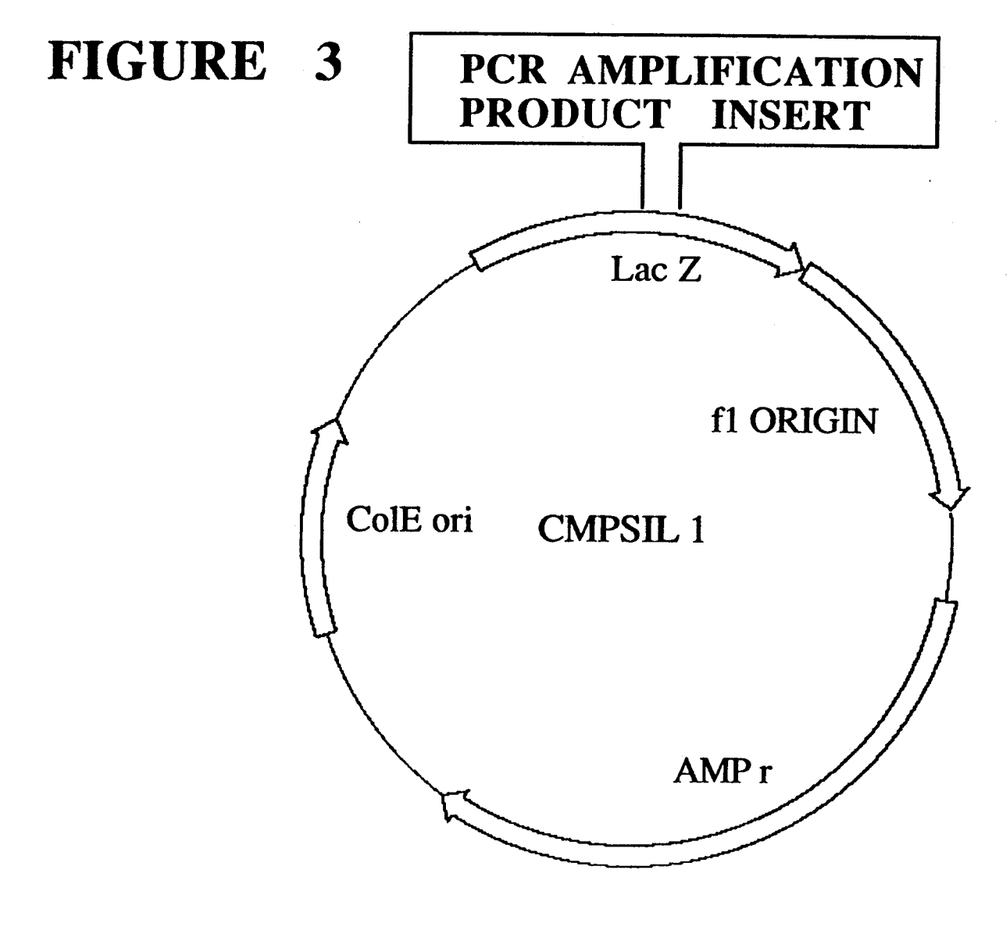
FIG. 3 is a schematic diagram showing the major features of phagemid CMPSIL-1. The PCR amplification product insert from FIG. 2 is shown at the top. The orientations of the insert and other genes are also shown.

One clone which produced higher CMP-NeuAc synthetase was isolated and designated as strain SIL-B3 and the phasemid contained therein designated CMPSIL-1 (FIG. 3). Phagemid CMPSIL-1 was isolated from strain SIL-B3 using a plasmid isolation kit (Qiagen Inc., Studio City, Calif.) and transformed to E. coli Sure competent cells (Strategene Co., San Diego, Calif.). Transformed cells were plated on LB agar plates containing 250 μg/mL ampicillin and screened for high enzyme production using the ELISA assay. One strain, designated E. coli SIL-S22, produced about 100 units of CMP-NeuAc synthetase activity per liter of culture broth. This production of CMP-NeuAc synthetase is over 1000 times greater than the amount of CMP-NeuAc synthetase produced by wild-type, non-transformed E. coli and over 30 times greater than the amount of CMP-NeuAc synthetase produced by the transformed cells described by Zapata et al., *J. Biol. Chem.* 264(25):14769 (1989).

*E. Coli* strain SIL-S22 were grown on LB-rich medium containing 250 μg/mL ampicillin to mid-logarithmic phase ($OD_{660}$ about 0.6-0.7) and induced with 0.5 mM IPTG for 10 hours at 30° C. The culture broth was centrifuged at 10,000 x g for 20 minutes at 4° C. and the pellet was washed with a buffer containing 0.2 M Tris (pH 7.5), 0.2 mM dithiothreitol and 20 mM $MgCl_2$. After washing, the cell pellet was resuspended in the same buffer and disrupted by a French pressure cell at 16,000 $lb/in^2$ and centrifuged at 23,000 x g for 60 minutes. The resulting supernatant was for enzyme activity assay according to the method of Vann et al., J. Biol. Chem., 262:17556 (1987) except that the developed color was extracted with cyclohexanone.

The enzyme was incubated in a 250 μl buffer containing 5.5 mM CTP, 2.8 mM N-acetylneuraminic acid, 0.2 M Tris, 20 mM MgCl₂ and 0.2 mM DTT, pH 9.0. After the mixture was incubated at 37° C. for 30 minutes, 50 μl of 1.6 M NaBH₄ was added to destroy excess NeuAc at room temperature for 15 minutes. The mixture was then put in ice bath and 50 μl of H₃PO₄ was added to destroy NaBH₄. The mixture was kept at 0° C. for 5 minutes then incubated at 37° C. for 10 minutes to cleave the phosphoester bond of the formed CMP-N-acetylneuraminic acid. The free N-acetylneuraminic acid was oxidized with 50 μl of 0.2 M NaIO₄ at room temperature for 10 minutes, and 400 μl of 4 percent NaAsO₂ in 0.5 N HCl was added. The solution mixture was then transferred to a test tube containing 1 ml of 0.6 percent thiobarbituric acid in 0.5 M Na₂SO₄, and heated in boiling water for 15 minutes. After the solution was cooled, 1 ml of the solution was taken out and mixed with 1 ml of cyclohexanone. The mixture was shaken and centrifuged, and the upper layer was taken for the measurement at 549 nm.

CMP-NeuAc was isolated by affinity chromatography using the anti-decapeptide antibody or Orange A (Amicon C., Danvers, MA) as ligand followed by gel filtration. Huse et al., *Science*, 246:1275 (1989). The cell free extract (30 mL) obtained as described above was passed through an Orange A Dye column (1.5 mg/ml gel, 3cm×30cm) and washed with 200 ml of Tris buffer (0.2 M Tris, 0.2 mM DTT and 2 mM MgCl₂, pH 7.5). The enzyme was eluted with a linear gradient from 0 M KCl to 1 M KCl in the same buffer. The active fraction was pooled and concentrated to 5 ml by ultrafiltration. The concentrated enzyme solution was then passed through an FPLC gel filtration column (Superose 12 h 10/30, Pharmacia Co.) at a flow rate of 0.2 ml/minute and the active fractions were collected. The protein concentration was determined by BCA assay kit (Pierce Co., Rockford, Ill.). The purity of the protein was judged by SDS PAGE (Phastsystem, Pharmacia Co.).

The foregoing is intended as illustrative of the present invention but not limiting. Numerous variations and modifications can be affected without departing from the true spirit and scope of the invention.

What is claimed is:

1. A method of synthesizing a sialylated glycosyl compound comprising reacting in an aqueous buffered solvent free of chelators that bind $Mg^{+2}$ or $Mn^{+2}$ at a temperature of about 15° C. to about 40° C. in the presence of each other:

a sialic acid;

a glycosyl compound:

a CMP-sialic acid regenerating system that comprises CMP, a nucleoside triphosphate, a phosphate donor and catalytic amounts of an isolated and purified kinase to transfer a phosphate group from said phosphate donor and an isolated and purified nucleoside monophosphate kinase;

a pyrophosphate scavenger and;

catalytic amounts of an isolated and purified CMP sialic acid synthetase and an isolated and purified sialyl transferase having substrate specificity for said glycosyl compound.

2. The method according to claim 1 wherein the glycosyl compound is selected from the group consisting of a monosaccharide, an oligosaccharide, a polysaccharide, a glycoprotein and a glycolipid.

3. The method according to claim 1 wherein the nucleoside triphosphate is ATP.

4. The method according to claim 1 wherein the phosphate donor is phosphoenolpyruvate.

5. The method according to claim 1 wherein the kinase is pyruvate kinase.

6. The method according to claim 1 wherein the CMP-sialic acid synthetase is obtained from *E. Coli* having the ATCC accession No. 68531.

7. The method according to claim 1 wherein the sialyl transferase is selected from the group consisting of 2→3 transferase, a 2→4 transferase, a 2→6 transferase and a 2→8 transferase.

8. The method according to claim 7 wherein the 2→3 transferase is Siaα2→3Gal.

9. The method according to claim 7 wherein the 2→4 transferase is Siaα2→4Gal or Siaα2→4GlcNAc.

10. The method according to claim 8 wherein the 2→6 transferase is Siaα2→6Gal, Siaα2→6GalNAc or 2→6GlcNAc.

11. The method according to claim 7 wherein the 2→8 transferase is Siaα2→8Sia.

12. The method according to claim 1 wherein the pyrophosphate scavenger is an inorganic pyrophosphatase.

13. The method according to claim 1 wherein said reaction is carried out under argon at about 25° C. for about 48 hours.

14. The method according to claim 1 further comprising the step of isolating said sialylated glycosyl compound.

15. A method of synthesizing sialyl N-acetyllactosamine comprising mixing N-acetyllactosamine, neuraminic acid, CMP, ATP, phosphoenolpyruvate, KCl, MgCl$_2$, MnCl$_2$, and catalytic amounts of nucleoside mono-phosphate kinase (EC 2.7.4.4), pyruvate kinase (EC 2.7.1.40), inorganic pyrophosphatase (EC 3.6.1.1), CMP-NeuAc synthetase (EC 2.7.7.43) and Siaα2→6Gal transferase (EC 2.4.99.1) with an aqueous buffer at pH 7.5 to form a reaction mixture and maintaining the reaction mixture under argon at about 25° C. for a period of time sufficient to deplete said neuraminic acid.

16. The method according to claim 15 further comprising the step of isolating said sialyl N-acetyllactosamine.

17. A composition for use in sialylating a glycosyl compound comprising a buffered aqueous solution free of chelators that bind mg$^{+2}$ or Mn$^{+2}$, said solution also containing:
 a sialic acid;
 a CMP-sialic acid regenerating system that comprises CMP, a nucleoside triphosphate, a phosphate donor and catalytic amounts of an isolated kinase to transfer a phosphate group from said phosphate donor and an isolated purified nucleoside monophosphate kinase;
 a pyrophosphate scavenger; and
 a catalytic amount of an isolated and purified CMP sialic acid synthetase.

18. The composition according to claim 17 further comprising a catalytic amount of a sialyl transferase having substrate specificity for said glycosyl compound.

19. The composition according to claim 17 wherein the nucleoside triphosphate is ATP.

20. The composition according to claim 17 wherein the phosphate donor is phosphoenolpyruvate.

21. The composition according to claim 17 wherein the kinase is pyruvate kinase.

22. The composition according to claim 17 wherein the CMP-sialic acid synthetase is obtained from *E. coli* having the ATCC accession No. 68531.

23. The composition according to claim 18 wherein the sialyl transferase is selected from the group consisting of a 2→3 transferase, a 2→4 transferase, a 2→6 transferase and a 2→8 transferase.

24. The composition according to claim 17 wherein the pyrophosphate scavenger is an pyrophosphatase.

* * * * *